United States Patent [19]

Liauw et al.

[11] 4,374,945

[45] Feb. 22, 1983

[54] THIOGLYCOLATE AND THIOPROPIONATE SECONDARY STABILIZERS

[75] Inventors: Koei-Liang Liauw, Wyckoff; Michael H. Fisch, Wayne, both of N.J.

[73] Assignee: Witco Chemical Corporation, New York, N.Y.

[21] Appl. No.: 242,741

[22] Filed: Mar. 11, 1981

[51] Int. Cl.³ .............. C07D 407/12; C07D 303/42; C07D 303/44; C08K 5/58; C08K 5/57; C08K 5/56; C08K 5/36

[52] U.S. Cl. .................................. 524/114; 524/175; 524/178; 524/180; 524/397; 524/399; 524/400; 549/557

[58] Field of Search .................. 260/45.8 A, 45.85 H, 260/45.85 S, 348.43; 560/152, 154; 549/557; 524/178, 180, 397, 399, 400, 114, 175; 252/400 R, 406

[56] References Cited

U.S. PATENT DOCUMENTS

| | | | |
|---|---|---|---|
| 2,416,052 | 2/1947 | Gribbins | 560/152 |
| 3,542,725 | 11/1970 | Kopacki et a. | 260/45.75 |
| 3,564,076 | 1/1971 | Kauder | 260/45.85 S |
| 3,637,809 | 1/1972 | Kleiner | 260/45.85 S |
| 3,839,507 | 10/1974 | Hechenbleikner et al. | 260/928 |
| 3,925,246 | 12/1975 | Coates et al. | 252/400 |
| 4,254,020 | 3/1981 | Kline | 260/45.85 H |

FOREIGN PATENT DOCUMENTS 654454  6/1947  United Kingdom ............... 560/154

*Primary Examiner*—V. P. Hoke
*Attorney, Agent, or Firm*—Albert L. Gazzola; Morton Friedman

[57] ABSTRACT

Certain substituted thioglycolates and thiopropionates were found useful as secondary stabilizers for polymers, particularly polyvinyl chloride, when used in conjunction with metal octanoates, such as zinc octanoate, as the primary stabilizer. The specific thioglycolates and thiopropionates are those formed by thio adducts to the double bond of a monomer, such as the product of reacting isooctyl thioglycolate with glycidyl acrylate, to provide isooctyl S-2(glycidyloxycarbonyl)ethyl thioglycolate, as an example.

17 Claims, No Drawings

THIOGLYCOLATE AND THIOPROPIONATE SECONDARY STABILIZERS

FIELD OF THE INVENTION

This invention relates to secondary stabilizers for polymers. Specifically, this invention relates to certain thioglycolate and thiopropionate stabilizers for vinyl halide resins.

BACKGROUND AND DISCUSSION OF PRIOR ART

Heretofore, generally undesirable quantities of cadmium-based stabilizers were found useful as stabilizers for vinyl polymers, particularly polyvinyl chloride. The art sought to avoid the extensive use of large quantities of cadmium-based stabilizers, and thus sought other possible stabilizers for vinyl halide resins.

In the patent to Coates, U.S. Pat. No. 3,925,246, granted Dec. 9, 1975, there are disclosed certain sulfur containing esters for use as costabilizers with organotin stabilizers for halogen containing resins.

Heckenbleikner, et al, U.S. Pat. No. 3,839,507, granted Oct. 1, 1974, disclose thiophosphate and thiophosphite esters as antioxidants and stabilizers against heat and light for halogen containing resins.

Kopacki, et al. U.S. Pat. No. 3,542,725, disclose certain thiol stabilizers derived from thiol acids for vinyl polymers.

While such prior art stabilizer systems were somewhat successful, the prior art desired a more effective polyvinyl halide stabilizer system.

It is, therefore, a principal object of the present invention to provide an effective stabilizer for polymers, particularly the halogen containing resins.

It is a further object of the present invention to proide a stabilizer as aforesaid which avoids the extensive use of cadmium compounds.

It is a still further object of the present invention to provide a novel costabilizer system which is highly effective for vinyl halide resins.

It is a still further object of the present invention to provide a stabilizer which is readily incorporated in and highly effective in flexible polyvinyl chloride resins.

DESCRIPTION OF THE PREFERRED EMBODIMENTS

Broadly speaking, the present invention comprises a polymer stabilizer comprising a compound having the following general formula:

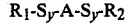

wherein:
A is $(CH_2)_x-O_n-(CH_2)_x$
x is 0 to 2; n is 0 or 1;
y is 0 or 1, with the proviso that at least one y is 1;
$R_1$ is

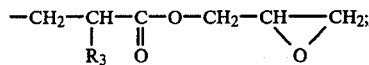

With $R_3$ being a lower alkyl or hydrogen; and $R_2$ is $R_1$, lower alkyl, or carbalkoxylower alkyl. $R_3$ may preferably be a $C_1$ to $C_6$ lower alkyl or hydrogen, and $R_2$ may preferably be a $C_1$ to $C_{12}$ lower alkyl.

In another aspect, the present invention comprises certain thioglycidyl esters as stabilizers for halogen containing resins, and the present invention recognizes the use of certain S-substituted glycidyloxycarboxyl compounds as stabilizers.

In another aspect, the present invention recognizes a certain novel secondary stabilizer system. By the terms "secondary stabilizer" as used hereinbefore and throughout the specification and claims, it is meant a stabilizer used in conjunction with another stabilizer.

Thus, in a still more specific aspect, the present invention is a polymer stabilizer system comprising the combination of certain thioglycolates and thiopropionates with known metal stabilizers, such as Group II metal octanoates, including in particular the calcium, barium and zinc carboxylates such as stearates, benzoates, phenates and octanoates, and the like, as known in the art.

The stabilizers of the present invention may be prepared by the addition of a mercaptan to a glycidyl acrylate.

The mercaptans useful pursuant to the present invention include the alkyl ($C_1$ to $C_{12}$) e.g. ethyl mercaptan, octyl mercaptan, lauryl mercaptan, and the like; alkyl esters (e.g. alkyl thioglycolate, butyl, hexyl, lauryl and isooctyl thioglycolate and thiopropionates, and the like); di-mercaptans (e.g. 1,2-ethane-dithiol) and the alkyl esthers useful in the present invention include 2-mercaptoethyl ether.

The glycidyl acrylates useful in the present invention include by way of example, the methacrylates as well.

Those primary stabilizers, useful in the present invention include not only the metal octanoates but a broad range of organo-metal stabilizers, specifically including those wherein the metal is one selected from Ca, Ba, Zn and Sn. Such suitable primary stabilizers pursuant to the present invention include a broad range of organo metal compounds such as butyl and octyl tin cyclic thioglycolate; the organo-metallic phosphites; and organo-metallic salts of fatty acids.

Other primary stabilizers can contain an epoxy compound, such as esters of epoxidized oleic acid, and other epoxidized compounds.

It was surprisingly found that when the aforesaid thioglycolates and thiopropionates were employed in combination with metal octanoates, such as barium, zinc, or tin octanoate, this costabilizer system provided a synergistic effect.

The present invention provides stabilization for polymeric materials comprising a halogen containing resin. The total stabilizer composition of the invention is usually in an amount of 0.1 to 10% by weight, preferably 1 to 8%, especially 1.1 to 6% (based on the weight of the resin). Typically, the Group II metal octanoate primary stabilizer is present within the range of 0.25 to about 10 parts by weight per 100 parts of resin, and the secondary stabilizer is present within the range of about 0.01 to 5 parts per 100 parts of the resin.

The resin normally contains at least 40% by weight of chloride. Usually it will be a polymer or co-polymer of vinyl chlorine or vinylidene chloride but post-halogenated polyvinyl chloride or post-halogenated polyolefins, such as polyethylene, e.g. post chlorinated compounds, may be employed if desired. Suitable monomers which may form such copolymers with vinyl chloride and vinylidene chloride include, for example, acrylonitrile, vinyl acetate, methyl methacrylate, diesters of fumaric acid and maleic acid, ethylene, propylene and lauryl vinyl ether and these co-monomers may be present in an amount of up to 25% to the total weight of monomers co-polymerized.

In the practice of the invention, the stabilizers may be mixed with the resin in the conventional manner, for example, by milling with the resin on heated rolls at 100°–160° C., e.g. about 150° C., although higher temperatures may be used when convenient, or by being mixed with particles of the polymer and then melting and extruding the mixture or by adding the stabilizer to a liquid resin.

The barium or zinc octanoate may be employed in either plasticized resin compositions, for example those plasticized with carboxylic ester plasticizers, e.g. di-2-ethylhexyl phthalate, dibutyl sebacate or diisooctyl phthalate or with phosphate esters such as tri (alkyl-phenyl) phosphates or may be employed in rigid compositions. Preferably and advantageously, the present stabilizer and co-stabilizer system are employed with and are highly effective with flexible PVC resins, plasticized compositions where the amount of plasticizers present is normally greater than 50% by weight of the polymeric material and is often greater than 100% on that basis; amounts of 30–150% are often used.

In addition to the stabilizers, the compositions of the invention may also contain conventional additives, e.g. pigments, fillers, dyes and ultraviolet absorbing agents.

The invention is illustrated in the following Examples:

EXAMPLE I

Isooctyl thioglycolate (83 g; 0.4 mole) was reacted at 30°–35° C., without solvent or catalyst, with glycidyl acrylate (128 g; 0.4 mole) to give isooctyl S-2-(glycidyloxycarbonyl)-ethyl thioglycolate, according to the following reaction:

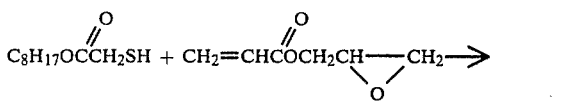

The produce thioglycolate had a saponification number of 325.3 (theoretical 337.5) and contains 4.72% oxirane oxygens by weight (theoretical 4.81%).

EXAMPLE II

1-Octanethiol, 71 g (0.5 mole), was reacted with glycidyl acrylate, 62 g (0.5 mole), at 50°–70° C., to give glycidyl 4-thialaurate according to the following reaction:

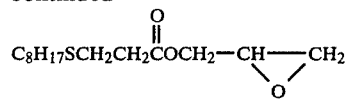

The product had a saponification number of 203.3 (theoretical 204.5) and contains 5.68% oxirane oxygen by weight (theoretical 5.83%).

EXAMPLE III

Isooctyl thioglycolate, 67.9 g (0.33 mole), was reacted with glycidyl methacrylate, 47.2 g (0.33 mole), at 40°–50° C., to give isooctyl S-(2-glycidyloxycarbonyl)-propyl thioglycolate according to the following reaction:

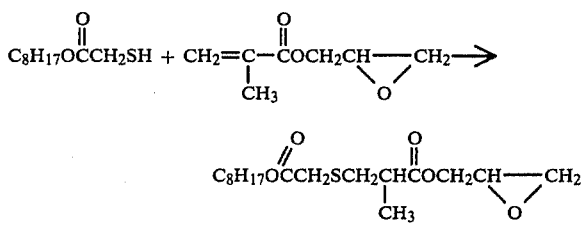

The produce had a saponification number of 276.7 (theoretical 323.8), and contains 4.33% oxirane oxygen by weight (theoretical 4.62%).

EXAMPLE IV 1,2-ethanedithiol, 14.4 g (0.15 moles), was reacted with glycidyl acrylate, 39.2 g (0.31 mole) at 25°–30° C., to give diglycidyl, 4,7-dithiasebacate according to the following reaction:

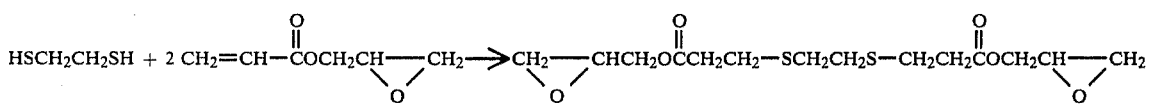

The product had a saponification number of 318.9 (theoretical 320.4), and contains 8.89% oxirane oxygen by weight (theoretical 9.14%).

EXAMPLE V

Isooctyl 3-mercaptopropionate, 43.2 g (0.2 mole), was reacted with glycidyl acrylate, 25.3 g (0.2 mole), at 40°–60° C., to give isooctyl S-2 (glycidyloxycarbonyl-)ethyl thiopropionate according to the following reaction:

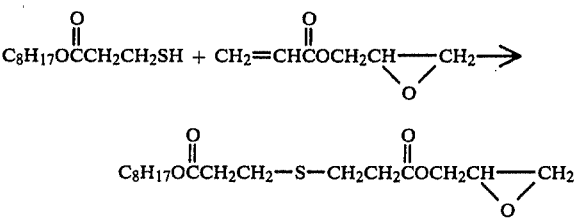

The product had a saponification number of 325.3 (theoretical 323.8), and contains 4.56% oxirane oxygen by weight (theoretical 4.62%).

EXAMPLE VI 2-mercaptoethyl ether, 18.3 g (0.13 mole), was reacted with glycidyl acrylate, 34 g (0.26 mole), at 25°–35° C., to give diglycidyl 4,10-dithia-7-oxatridecanedioate according to the following reaction:

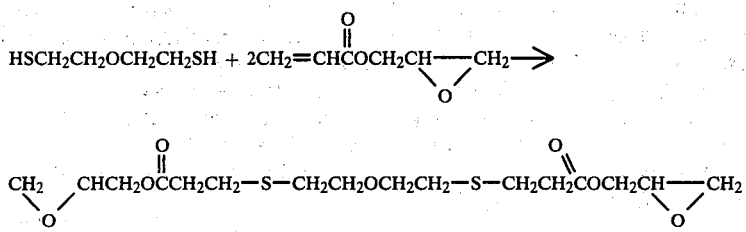

The product had a saponification number of 278.8 (theoretical 284.6) and contains 7.96% oxirane oxygen by weight (theoretical 8.12%).

The following resin formulations were prepared and tested using the stabilizers prepared in the foregoing Examples.

The stabilizers of the above Examples were mixed in a PVC resin on a two roll mill to form a homogeneous sheet, and sheeted off. Strips were cut from the sheet and tested in an oven at 350° F., and if tin is present, at 375° F. for two hours to determine heat stability. Pieces of each strip were removed at 15 minute intervals and affixed to cards to show the progressive heat deterioration.

The control sample for all the following tests was epoxidized soy bean oil (Drapex 6.8) which was used in the below stated weights, and compared with the compounds of the Examples, which compounds are denoted by the Example Nos. hereinbelow:

| TEST I | |
|---|---|
| Component | Parts |
| PVC resin | 100 |
| Dioctyl phthalate | 37 |
| *Ba/Zn stabilizer containing phosphite | 3.0 |
| Stearic acid | 0.25 |
| Example I Product | 2–3 |

The Test I was tested at 2.0 parts when compared to the control at 3.0 parts, and Example 1 compound improved early color even at the lower level, and also improved length.

| TEST II | |
|---|---|
| Component | Parts |
| PVC resin | 100 |
| Dioctyl phthalate | 37 |
| Dioctyltin thioglycolate | 0.5 |
| Stearic acid | 0.25 |
| Example I Product | 2–3 |

At equal test levels, the product of Example I gave greatly improved color and length.

| TEST III | |
|---|---|
| Component | Parts |
| PVC resin | 100 |
| Dioctyl phthalate | 37 |
| Stearic acid | 0.25 |
| Dioctyltin thioglycolate | 0.5 |
| Product of Example II | 2.0 |

At equal test levels of 2.0 parts, product of Example II showed improved color and length compared with the control.

| TEST IV | |
|---|---|
| Components | Parts |
| PVC resin | 100 |
| Dioctyl phthalate | 37 |
| Stearic acid | 0.25 |
| *Ba/Zn stabilizer containing phosphite | 2.0 |
| Example II Product | 2.0 |

At a 2.0 parts test level, Example II compound gave as much extension as the control at 3.0.

| TEST V | |
|---|---|
| Component | Parts |
| PVC resin | 100 |
| Dioctyl phthalate | 37 |
| Stearic acid | 0.25 |
| *Ba/Zn stabilizer containing phosphite | 2.0 |
| Example II Product | 2.0 |

At a 2.0 parts test level, the Example II compound gave better early color than the control at 3.0 parts.

| TEST VI | |
|---|---|
| Component | Parts |
| PVC resin | 100 |
| Dioctyl phthalate | 37 |
| *Ba/Zn stabilizer containing phosphite | 3.0 |
| Stearic acid | 0.25 |
| Example III Product | 3.0 |

At equal levels, Example III compound gave better length than the control. The early color was marginally better than the control.

| TEST VII | |
|---|---|
| Component | Parts |
| PVC resin | 100 |
| Dioctyl phthalate | 37 |
| *Ba/Zn stabilizer containing phosphite | 3.0 |
| Stearic acid | 0.25 |

TEST VII

| Component | Parts |
|---|---|
| Example IV Product | 1.0 |

*Mark ® RFD, Argus Chemical Corp., Brooklyn, N.Y.

The test VII showed equal length and comparable color to the control, wherein the control was at three times the level than the Example IV compound.

As can be seen, the compounds of the present invention in combination wih metal stabilizers provide improved stabilization of halogen containing resins.

The embodiments of the invention in which an exclusive property and privilege is claimed are defined as follows:

1. A thioglycidyl ester compound having the formula $R_1-S_y-A-S_y-R_2$, wherein
A is $(CH_2)_x-O_n-(CH_2)_x$
x is 0 to 2; n is 0 or 1;
y is 0 or 1, with the proviso that at least one y is 1;
$R_1$ is

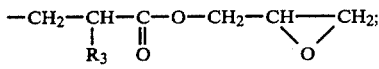

with $R_3$ being alkyl having one to about six carbon atoms or hydrogen; and $R_2$ may be $R_1$; an alkyl having one to about twelve carbon atoms, or carbalkoxy having one to about twelve carbon atoms in the alkoxy group.

2. The compound of claim 1, wherein $R_3$ is hydrogen.

3. The compound of claim 1, wherein said compound is isooctyl S-2(glycidyloxycarbonyl)ethylthioglycolate.

4. A stabilizer composition for a vinyl halide, polymer, comprising a primary vinyl halide polymer stabilizer selected from the group consisting of an organometallic compound, an epoxy compound and a metal carboxylate and a thioglycidyl ester compound having the formula:

wherein:
A is $(CH_2)_x-O_n-(CH_2)_x$
x is 0 to 2; n is 0 or 1;
y is 0 or 1, with the proviso that at least one y is 1;
$R_1$ is

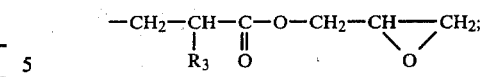

with $R_3$ being alkyl having one to about 6 carbon atoms or hydrogen; $R_2$ is $R_1$, lower alkyl having one to about 12 carbon atoms, or carbalkoxy having one to about 12 carbon atoms in the alkoxy group.

5. The stabilizer composition of claim 4, wherein said thio-glycidyl ester compound is the reaction product of a mercaptan and a glycidyl acrylate.

6. The sabilizer composition of claim 4, wherein $R_3$ is hydrogen.

7. The stabilizer composition of claim 4, said primary stabilizer comprising a metal octanoate.

8. The stabilizer composition of claim 7, said metal being one selected from Ca, Ba, Zn and Sn.

9. The stabilizer composition of claim 4, wherein said thioglycidyl ester compound is isooctyl S-2-(glycidyloxycarbonyl)ethyl thioglycolate.

10. The stabilizer composition of claim 4, wherein said thioglycidyl ester compound is glycidyl 4-thialaurate.

11. The stabilizer composition of claim 4, wherein said thioglycidyl ester compound is isooctyl S-2-(glycidyloxycarbonyl)ethyl thiopropionate.

12. The stabilizer composition of claim 4, wherein said thioglycidyl ester compound is diglycidyl 4,7-dithiasebacate.

13. The stabilizer composition of claim 4, wherein said thioglycidyl ester compound is diglycidyl 4,10-dithia-7-oxatridecanedioate.

14. The stabilizer composition of claim 5, wherein said thioglycidyl ester compound is isooctyl S-(2-glycidyloxycarbonyl)propyl thioglycolate.

15. A stabilized halogen containing resin composition comprising 0.1 to 10% based on the weight of the resin of a stabilizer composition according to claim 4.

16. A stabilized composition according to claim 15 in which the halogen containing resin is a polymer of vinyl chloride.

17. The stabilized composition of claim 15 in which said primary stabilizer is present within the range of 0.25 to 10 parts by weight and the thioglycidyl ester stabilizer is present within the range of 0.01 to 5 parts by weight, based on the weight of the resin.

* * * * *